United States Patent
Wong et al.

(10) Patent No.: US 6,964,962 B2
(45) Date of Patent: Nov. 15, 2005

(54) COMBINATIONS OF REBOXETINE AND NEUROLEPTIC AGENTS

(75) Inventors: Erik Ho Fong Wong, Portage, MI (US); Christopher C. Gallen, Wynnewood, PA (US); Torgny Svensson, Lidingö (SE)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/035,100

(22) Filed: Dec. 28, 2001

(65) Prior Publication Data

US 2002/0156067 A1 Oct. 24, 2002

Related U.S. Application Data

(60) Provisional application No. 60/259,286, filed on Jan. 2, 2001.

(51) Int. Cl.$^7$ ............... A61K 31/505; A61K 31/5375; A61K 31/5513
(52) U.S. Cl. ............... 514/239.2; 514/220; 514/259.41
(58) Field of Search ............... 514/239.2, 220, 514/259.41

(56) References Cited

U.S. PATENT DOCUMENTS 3,505,451 A    4/1970  Burnings et al.

FOREIGN PATENT DOCUMENTS

| EP | 0 830 864 A1 | 3/1998 |
|----|--------------|--------|
| EP | 0 966 967 A2 | 12/1999 |
| FR | 2 722 099 A1 | 7/1994 |
| WO | WO 99/61014  | 12/1999 |

OTHER PUBLICATIONS

Koch et al, Eur. J. Clin. Pharmacol. (56, No. 6–7, A10, 2000) (abstract).*
E. Aragues, et al., "Reboxetine in Negative Symptoms of Schizophrenia", European Psychiatry, 2000, pp 426S, Abstract Only.
G. Schutz, et al., "Reboxetine Add on Therapy to Haloperidol in The Treatment of Schizophrenia: a Preliminary Double–blind Randomized Placebo–controlled Study", International Clinical Psychopharmacology, 2001, pp 275–278, vol. 16, No. 5.
E. Spina, et al, "No Effect of Reboxetine on Plasma Concentrations of Clozapine, Risperidone, and Their Active Metabolites", 2001, pp675–678, vol. 23 No. 6.

* cited by examiner

Primary Examiner—Phyllis G. Spivack
(74) Attorney, Agent, or Firm—Charles W. Ashbrook; David R. Kurlandsky

(57) ABSTRACT

A composition comprising:
(a) a pharmaceutically effective amount of reboxetine; and selected from the group consisting of clozapine, olanzapine, risperidone and mixtures thereof
(b) a pharmaceutically effective amount of one or more neuroleptic agents or a pharmaceutically effective salt thereof is provided.

2 Claims, No Drawings

COMBINATIONS OF REBOXETINE AND NEUROLEPTIC AGENTS

CROSS-REFERENCE TO RELATED APPLICATION

This application claims the benefit of the following provisional application: U.S. Ser. No. 60/259,286, filed Jan. 2, 2001, under 35 USC 119(e)(i), which is incorporated herein by reference in its entirety.

BACKGROUND OF THE INVENTION

1. Field of the Invention

This invention describes new treatments that should provide for relief from several nervous system disorders with reduced side effects, and it involves the administration of a norepinephrine reuptake inhibitor, preferably a selective norepinephrine reuptake inhibitor such as the drug reboxetine, in combination with a neuroleptic agent (typical or atypical antipsychotic agents). In particular, the combination is to be used to treat schizophrenia.

2. Technology Description

The introduction of tricyclic antidepressants in the early 1960s has provided a major advance in the treatment of neuropsychiatric disorders. Reactive and endogenous depressions, diagnoses formerly carrying grave prognostic implications, have become, with the introduction of the tricyclics, manageable disorders with a much smaller toll on the patient and the society as a whole.

The early tricyclic compounds were reuptake inhibitors of all the catecholamines released in the synaptic cleft, thus resulting in prolongation and enhancement of the dopamine (DA), noradrenaline (NA) and serotonin (5-hydroxytryptamine=5-HT) action. Lack of selectivity also causes undesired side effects particularly on the acetylcholine (especially the muscarinic component), and histamine mediated neurotransmission.

Because of these unwanted pharmacodynamic activities, cognitive impairment, sedation, urinary and gastrointestinal tract disturbances, and increased intraocular pressure were limiting factors in the clinical use of these compounds and often required discontinuation of treatment. Of utmost concern were also the cardiac toxic effects and the proconvulsant activity of this group of drugs.

More recently, selective reuptake inhibitors for serotonin (SSRI) have been introduced with definite advantages in regard to fewer side effects without loss of efficacy. Fluoxetine is an example of such an inhibitor that has had a great amount of commercial success.

Another class of compounds that has been proposed for use in the treatment of depression is selective norepinephrine reuptake inhibitors. Lower-than-normal levels of norepinephrine are associated with a variety of symptoms including lack of energy, motivation, and interest in life. Thus, a normal level of norepinephrine is essential to maintaining drive and capacity for reward. These neurotransmitters travel from the terminal of a neuron across a small gap (i.e., the synaptic cleft) and bind to receptor molecules on the surface of a second neuron. This binding elicits intracellular changes that initiate or activate a response or change in the postsynaptic neuron. Inactivation occurs primarily by transport (i.e., reuptake) of the neurotransmitter back into the presynaptic neuron. Abnormality in noradrenergic transmission results in various types of depression, mental, behavioral, and neurological disorders attributed to a variety of symptoms including a lack of energy, motivation, and interest in life. See generally, R. J. Baldessarini, "Drugs and the Treatment of Psychiatric Disorders: Depression and Mania" in *Goodman and Gilman's The Pharmacological Basis of Therapeutics*, McGraw-Hill, NY, N.Y., pp. 432–439 (1996).

Examples of norepinephrine reuptake inhibitors (both selective and not selective) include, but are not limited to the following: tandamine (CAS 42408-80-0; U.S. Pat. Nos. 3,904,617; 4,118,394), pirandamine (CAS 42408-79-7; U.S. Pat. No. 3,995,052), ciclazindol (CAS 37751-39-6; U.S. Pat. No. 3,891,644; No. 3,957,819; No. 3,976,645), fluparoxan (U.S. Pat. No. 4,880,801), lortalamine (CAS 70384-91-7; U.S. Pat. No. 4,201,783), talsupram (CAS 21489-20-3), talopram (CAS 7182-51-6), prindamine, nomifensine (U.S. Pat. No. 3,577,424), viloxazine (U.S. Pat. No. 3,712,890), tomoxetine (U.S. Pat. No. 4,314,081), duloxetine (U.S. Pat. No. 5,023,269), venlafaxine (U.S. Pat. No. 4,535,186), milnacipran (U.S. Pat. No. 4,478,836) and reboxetine (U.S. Pat. No. 4,229,449).

The term schizophrenia was first used in 1911 by Eugen Bleuler, a Swiss psychiatrist, to diagnose patients whose thought processes and emotional responses seemed to be disconnected. The term schizophrenia literally means split mind and many people still believe incorrectly that the condition causes a split personality (actually an uncommon problem involving dissociation). Schizophrenia is now used to describe a cluster of symptoms that typically includes delusions, hallucinations, disordered thinking, and emotional unresponsiveness. No clear-cut definition of schizophrenia exists even at this time and no single cause has been found to explain all aspects of this devastating syndrome. Most likely, the symptoms are triggered by a number of disease processes coupled with genetic factors and environmental stresses.

Chemical treatment for those suffering from schizophrenia include the use of neuroleptic agents (sometimes referred to as antipsychotic agents) of either the typical or atypical type.

Typical neuroleptic agents are those that block receptors of the neurotransmitter dopamine. These medications are also referred to as neuroleptic drugs, because they can cause a number of neurologic side effects. The first drug of this type used for treating schizophrenia was chlorpromazine (Thorazine; U.S. Pat. No. 2,645,640). Many other antipsychotic drugs are now available, the most popular being haloperidol (Haldol; U.S. Pat. No. 3,438,991). Others include perphenazine (Trilafon; U.S. Pat. No. 2,766,235), thioridazine (Mellaril; dosage of 30-800 mg/day), mesoridazine (Serentil; U.S. Pat. No. 3,084,161), trifluoperazine (Stelazine; U.S. Pat. No. 2,921,069), and fluphenazine (Prolixin; U.S. Pat. No. 3058979). For the very severe active phase of schizophrenia, injections of an antipsychotic drug are often given every four to eight hours until the patient is calm. If possible, however, physicians prefer administering a drug orally. These drugs may be high- or low-potency. Generally, higher doses are used to treat acute episodes (e.g., 5 to 10 mg of haloperidol) and lower doses are given during periods of remission (e.g., 2 to 5 mg). However, new studies suggest starting haloperidol treatment with daily doses in the 4 to 5 mg range for two to three weeks. The beneficial impact of these drugs is greatest on psychotic symptoms, particularly hallucinations and delusions in the early and midterm stages of the disorder. In patients who are being treated for the first time, improvement in psychotic symptoms may be evident within one or two days of treatment, although the full benefit of the drug usually evolves over about six to eight weeks. Thought disturbances are reduced more gradually. Some estimates of poor responses to these drugs are as high as 40%. Antipsychotic drugs are also not very successful in reducing negative symptoms, although people often show less withdrawal and apathy because of the reduction in psychotic episodes. The most disturbing common side effects of high-dose or high-potency therapy of typical antipsychotic drugs are those known as extrapyramidal symptoms, which effect the nerves and muscles controlling movement and coordination. The most serious long term extrapyramidal effect of antipsychotic therapy is tardive dyskinesia, a condition associated with repetitive and involuntary movements, or tics, most often in the mouth, lips, and tongue and also in the legs, arms and trunk. Symptoms range from mild to severe, and sometimes interfere with eating and walking. They may not appear until the antipsychotic drugs have been taken for months or even years. A condition known as acute dystonia can occur shortly after taking antipsychotic drugs. This side effect causes abnormal muscle spasms, particularly sustained contortions of the neck, jaw, trunk, and eye muscles. High potency drugs (e.g., haloperidol, fluphenazine) cause less drowsiness and very low blood pressure but induce more extrapyramidal side effects. Low-potency drugs (e.g., chlorpromazine, thioridazine) are more sedating and side effects are not as acute. Nearly every neuroleptic drug can cause extrapyramidal side effects, however, which occur in up to 70% of patients taking these medications. After the drug is withdrawn, symptoms can sometimes persist for weeks or months. Women face a higher risk for these symptoms, and they increase with length of therapy and age. These medications can have adverse side effects on many organs and systems in the body. Sleepiness and lethargy commonly occur in the beginning of therapy, but usually decrease over time. Other side effects include dry mouth, eye problems, allergic reactions, temporary weight gain, and menstrual irregularities in women. A much more serious but rare side effect is the neuroleptic malignant syndrome, in which dangerously high body temperatures occur. Without prompt and expert treatment, this side effect can be fatal in 20% of those who develop it. Sometimes the effects of the drugs mimic schizophrenic symptoms, such as agitation, slow speech, and retarded movement, and so the physician may be tempted to increase the dosage.

Drugs known as atypical drugs (also referred to in this document as atypical neuroleptic or atypical antipsychotic agents) are rapidly changing treatment for schizophrenia, and many experts are now urging that they be used as the primary treatment for certain patients instead of the antipsychotics. Atypical drugs appear to be more effective than the neuroleptics, even in reducing negative symptoms and preventing relapse. They are rarely associated with the extrapyramidal side effects, particularly tardive dyskinesia. The most successful atypical drugs are able to simultaneously affect dopamine receptors and other neurotransmitters responsible for psychotic symptoms. Clozapine (U.S. Pat. No. 3,539,573), olanzapine (U.S. Pat. No. 5,229,382), and risperidone (U.S. Pat. No. 4,804,663) are currently the standard atypical drugs, but new medication that may be even more effective are becoming available. Clozapine (Clozaril) is the best known of these drugs. Clozapine was found to benefit up to half of patients with schizophrenia who did not respond to other types of treatments, and there is now substantial evidence of its superiority over typical drugs. It is particularly useful in younger people, although toxic side effects are common. Positive effects may not be evident for up to nine months. Clozapine has improved negative symptoms in short-term trials; longer ones are needed to see if the benefit is sustained. It may also reduce aggressive behavior and suicidal impulses. Although the drug does not appear to cause tardive dyskinesia, it does have other side effects including nasal congestion, drooling, low blood pressure, headache, sleeplessness, and significant weight gain. Serious side effects include seizures and, in up to 1% of cases, agranulocytosis—a potentially life-threatening decrease in the patient's white blood cells. When agranulocytosis develops, it usually does so within three months of treatment, peaking in the third month; if it hasn't appeared within six months, it most likely will not develop. Older women are at higher risk for this side effect. Agranulocytosis can be reversed if treatment with clozapine is stopped at once. It is important that people taking clozapine have their serum glucose level count monitored frequently, especially those with diabetes or a family history of diabetes. Although clozapine is more expensive than haloperidol, this extra expense may be offset by its greater efficacy, which results in fewer hospitalizations. Risperidone. Risperidone (Risperdal) is a dopamine receptor blocker that has shown benefit and even superiority in comparison to antipsychotics. It is now used by about 20% of schizophrenia patients. Like clozapine, risperidone may have a beneficial effect on negative symptoms. Risperidone may also improve verbal working memory, a common problem in schizophrenics. It has few extrapyramidal effects, although they can occur at higher doses. Common side effects include sleepiness, weight gain, and dizziness. Olanzapine. Olanzapine (Zyprexa) may be more effective in blocking the neurotransmitters serotonin and dopamine than is clozapine and have a much lower risk for seizures and agranulocytosis. Studies indicate it is at least as effective for acute symptoms and possibly more effective for negative ones than the typical neuroleptic drugs and that it has a very low risk for extrapyramidal symptoms. The drug may also be beneficial for patients who do not respond to neuroleptic drugs. A new study suggests that olanzapine also may be more effective than risperidone, particularly in its effect on negative symptoms, but more research is needed to confirm result. Like risperidone, olanzapine can cause sleepiness, weight gain, and dizziness. Other Atypical Drugs. Ziprasidone (U.S. Pat. No. 4,831,031) and quetiapine (Seroquel; U.S. Pat. No. 4,879,288), which has recently been approved by the FDA, are other promising new drugs. Ziprasidone affects serotonin as well as dopamine may also improve negative symptoms with limited extrapyramidal side effects. Sertindole (Serlect; U.S. Pat. No. 4,710,500) is another drug well into development. Although promising, reports of increased risk for sudden cardiac death are of some concern. Aripiprazole (U.S. Pat. No. 5,006,528) is another atypical drug in development.

Still other drugs for the treatment of schizophrenia include, but are not limited to the following typical and atypical neuroleptic agents: blonanserin (U.S. Pat. No. 5,021,421), iloperidone (EP 402644), perospirone (U.S. Pat. No. 4,745,117), raclopride (U.S. Pat. No. 4,789,683), sonepiprazole (U.S. Pat. No. 5,877,317), zotepine (U.S. Pat. No. 3,704,245), DU-127090, ORG-5222 (GB 1567862), SM-13496, amisulpride (U.S. Pat. No. 4,401,822), CP-361428, Lu 35-138, balaperidone (WO 94/00458), S-18327 (EP 811622), WAY-135452 (also known as DAB-452), eplivanserin (EP 373998), E-5842 (WO96/4287), SR-31742 (EP 461986), NE-100 (EP 641766), osanetant (EP512901, EP 673928), SR-141716 (EP 658546), SR-48692 (EP 477049), BSF-201640 (WO99/09015), BSF-190555 (WO95/07274), LAX-101a, sarizotan (EP 707007), CX-691 (U.S. Pat. Nos. 5,783,587, 5,891,876) and SB-271046 (WO98/27081).

Despite the above advances in the art, it would be desirable to develop a pharmaceutical composition that would have both the therapeutic benefits of the neuroleptic agents (typical or atypical) with a reduced side effects.

BRIEF SUMMARY OF THE INVENTION

In accordance with the present invention a novel pharmaceutical composition is provided. More specifically, the composition combines one or more norepinephrine reuptake inhibitors, more preferably one or more selective norepinephrine reuptake inhibitors with one or more neuroleptic agents (typical or atypical antipsychotic agents). The composition is considered to be particularly effective against schizophrenia.

A first embodiment of the present invention provides a composition comprising:

(a) a pharmaceutically effective amount of one or more norepinephrine reuptake inhibitors or a pharmaceutically effective salt thereof; and (b) a pharmaceutically effective amount of one or more neuroleptic agents or a pharmaceutically effective salt thereof.

In particularly preferred embodiments, component (a) comprises reboxetine in either its enantiomeric or racemic form.

Yet another embodiment of the present invention provides a method for treating or preventing diseases or disorders of the central nervous system comprising administering a therapeutically effective amount of the above composition to a mammal. In most instances, the mammal will be a human, and the disease or disorder to be treated is schizophrenia.

A further embodiment of the present invention comprises the use of the above composition to prepare a medicament for treating or preventing diseases or disorders of the central nervous system.

An object of the present invention is to provide novel composition having biological activity.

A further object of the present invention is to provide a method for treating or preventing diseases of the central nervous system by using the novel compositions of the present invention.

An additional object of the present invention is to provide an effective treatment for schizophrenia.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention provides a novel composition which is a combination of different chemical entities, more specifically, the first entity being a norepinephrine reuptake inhibitor, particularly a selective norepinephrine reuptake inhibitor and the second being a neuroleptic agent.

The first component is a norepinephrine reuptake inhibitor, with selective norepinephrine reuptake inhibitors being particularly preferred. This list of compounds includes, but is not limited to the following: tandamine, pirandamine, ciclazindol, fluparoxan, lortalamine, talsupram, talopram, prindamine, nomifensine, viloxazine, tomoxetine, duloxetine, venlafaxine, milnacipran and reboxetine, with reboxetine being particularly preferred.

Examples of pharmaceutically effective salts for the norepinephrine reuptake inhibitor include, but are not limited to salts prepared from pharmaceutically acceptable acids or bases, including organic and inorganic acids and bases. When the preferred compound of use is basic (for example reboxetine), salts may be prepared from pharmaceutically acceptable acids. Suitable pharmaceutically acceptable acids include acetic, benzenesulfonic (besylate), benzoic, p-bromophenylsulfonic, camphorsulfonic, carbonic, citric, ethanesulfonic, fumaric, gluconic, glutamic, hydrobromic, hydrochloric, hydroiodic, isethionic, lactic, maleic, malic, mandelic, methanesulfonic (mesylate), mucic, nitric, oxalic, pamoic, pantothenic, phosphoric, succinic, sulfuric, tartaric, p-toluenesulfonic, and the like. Examples of such pharmaceutically acceptable salts include, but are not limited to, acetate, benzoate, hydroxybutyrate, bisulfate, bisulfite, bromide, butyne-1,4-dioate, carpoate, chloride, chlorobenzoate, citrate, dihydrogenphosphate, dinitrobenzoate, fumarate, glycollate, heptanoate, hexyne-1, 6-dioate, hydroxybenzoate, iodide, lactate, maleate, malonate, mandelate, metaphosphate, methanesulfonate, methoxybenzoate, methylbenzoate, monohydrogenphosphate, naphthalene-1-sulfonate, naphthalene-2-sulfonate, oxalate, phenylbutyrate, phenylproionate, phosphate, phthalate, phylacetate, propanesulfonate, propiolate, propionate, pyrophosphate, pyrosulfate, sebacate, suberate, succinate, sulfate, sulfite, sulfonate, tartrate, xylenesulfonate, and the like.

In particularly preferred embodiments the selective norepinephrine reuptake inhibitor is reboxetine, 2-[α-((2-ethoxyphenoxy)benzyl]-morpholine, and its pharmaceutically acceptable salts, in either its enantiomeric (particularly the (S,S) enantiomer) or racemic form. Synthesis of racemic reboxetine is described in greater detail in U.S. Pat. No. 4,229,449. Individual stereoisomers of reboxetine can be obtained by resolution of the racemic mixture of enantiomers using conventional methods generally known by those skilled in the art. Such methods include, but are not limited to, resolution by simple crystallization and chromatographic techniques, for example, as set forth in GB 2,167,407. Other methods of preparation are described in U.S. Pat. Nos. 5,068,433 and 5,391,735. Reboxetine can be a free base form, or it can be in salt form, preferably the methanesulfonate salt (also called reboxetine mesylate). To the extent necessary for completion, the above patents are expressly incorporated by reference.

The selection of the dosage of the first component is that which can provide relief to the patient. As is well known, the dosage of this component depends on several factors such as the potency of the selected specific compound, the mode of administration, the age and weight of the patient, the severity of the condition to be treated, and the like. This is considered to be within the skill of the artisan and one can review the existing literature on the components to determine optimal dosing. To the extent necessary for completion, the synthesis of the components and dosages described in the patents or CAS documents referenced in the Technology Description portion of this document are expressly incorporated by reference Desirably, when reboxetine is selected as the active agent, the daily dose contains from about 0.1 mg. to about 10 mg. More preferably, each dose of the component contains about 0.5 to about 8 mg of the active ingredient, and even more preferably, each dose contains from about 0.5 to about 5 mg of the active ingredient. This dosage form permits the full daily dosage to be administered in one or two oral doses. This will allow for final formulations containing 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9. 2.0, 2.1, 2.2, 2.3, 2.4, or 2.5 mg of active. More than once daily or twice daily administrations (e.g., 3, 4, 5 or 6 administrations per day) are also expressly contemplated herein.

The average daily adult dosage of the other norepinephrine reuptake inhibitors is as follows. The dosages expressly include all numerical values, whole or fractional, within the stated range. Pediatric dosages may be less.

| Component | Average Daily Dosage (mg/day/patient) |
|---|---|
| Tandamine | 7.5 to 3750 |
| Pirandamine | 7.5 to 3750 |
| Ciclazindol | 5 to 500 |
| Fluparoxan | .75 to 750 |
| Lortalamine | 1 to 200 |
| Talsupram | 1 to 3750 |
| Talopram | 1 to 3750 |
| Prindamine | 1 to 3750 |
| Nomifensine | 1 to 80 |
| Viloxazine | 1 to 3750 |
| Tomoxetine | 1 to 200 |
| Duloxetine | 5 to 500 |
| Venlafaxine | 2 to 200 |
| Milnacipran | 7.5 to 75 |

The second component comprises one or more neuroleptic agents. These can include those which are typical antipsychotic agents and those which are atypical antipsychotic agents. Examples of such agents include, but are not limited to the following: chlorpromazine, haloperidol, perphenazine, thioridazine, mesoridazine, trifluoperazine, fluphenazine, clozapine, olanzapine, sonepiprazole, risperidone, ziprasidone, quetiapine, sertindole, aripiprazole, iloperidone, blonanserin, perospirone, zotepine, DU-127090, ORG-5222, SM-13496, amisulpride, raclopride, sonepiprazole, CP-361428, Lu 35-138, balaperidone, S-18327, WAY-135452 (also known as DAB-452), eplivanserin, E-5842, SR-31742, NE-100, osanetant, SR-141716, SR-48692, BSF-201640, BSF-190555, LAX-101a, sarizotan, CX-691 and SB-271046.

As is well known, the dosage and administrative regimen (i.e., one, two, three or more administrations per day) of the second component depends on the factors referred to in connection with the dosage selection of the first component. To the extent necessary for completion, the synthesis of the components and dosages described in the patents or CAS documents referenced in the Technology Description portion of this document are expressly incorporated by reference The average adult daily dosage of the neurolpetic agent is as follows. The dosages expressly include all numerical values, whole or fractional, within the stated range. Pediatric dosages may be less.

| Component | Average Daily Dosage (mg/day/patient) |
|---|---|
| Chlorpromazine | 10 to 150 |
| Haloperidol | .5 to 100 |
| Mesoridazine | 75 to 400 |
| Perphenazine | 5 to 100 |
| Thioridazine | 30 to 800 |
| Trifluoperazine | 1 to 50 |
| Fluphenazine | 2.5 to 100 |
| Clozapine | 25 to 500 |

-continued

| Component | Average Daily Dosage (mg/day/patient) |
|---|---|
| Olanzapine | 0.05 to 30 |
| Risperidone | .25 to 25 |
| Ziprasidone | 5 to 500 |
| Quetiapine | 25 to 800 |
| Sertindole | 1 to 500 |
| Aripiprazole | 7.5 to 750 |
| Sonepiprazole | .75 to 3750 |
| Blonanserin | .75 to 3750 |
| Iloperidone | .75 to 7500 |
| Perospirone | .5 to 1000 |
| Zotepine | 30 to 1000 |
| DU-127090 | .05 to 7500 |
| ORG-5222 | .75 to 750 |
| SM-13496 | .05 to 7500 |
| Amisulpride | 50 to 750 |
| Raclopride | 1 to 500 |
| CP-361428 | .05 to 7500 |
| Lu 35-138 | .05 to 7500 |
| Balaperidone | .75 to 7500 |
| S-18327 | .5 to 100 |
| WAY-135452 | .05 to 7500 |
| Eplivanserin | .1 to 2000 |
| E-5842 | 1 to 2000 |
| SR-31742 | .5 to 4000 |
| NE-100 | .1 to 100 |
| Osanetant | .5 to 4000 |
| SR-141716 | .5 to 4000 |
| SR-48692 | 1 to 1000 |
| BSF-201640 | 1 to 1000 |
| BSF-190555 | 1 to 500 |
| LAX-101a | .05 to 7500 |
| Sarizotan | 0.2 to 2000 |
| CX-691 | 1 to 400 |
| SB-271046 | 0.05 to 1000 |

Compositions of the present invention can conveniently be administered in a pharmaceutical composition containing the active components in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). To the extent necessary for completion, this reference is hereby incorporated by reference. The compositions of the present invention can be administered parenterally (for example, by intravenous, intraperitoneal or intramuscular injection), topically, orally, intranasally, intravaginally, or rectally, with oral administration being particularly preferred.

For oral therapeutic administration, the inventive composition may be combined with one or more excipients and used in the form of ingestible tablets, buccal tablets, troches, capsules, elixirs, suspensions, syrups, wafers, chewing gums, foods and the like. Such compositions and preparations should contain at least 0.1% of active compound. The percentage of the compositions and preparations may, of course, be varied and may conveniently be between about 0.1 to about 100% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active components may be incorporated into sustained-release preparations and devices including, but not limited to, those relying on osmotic pressures to obtain a desired release profile.

The inventive composition, containing the two active components, may be administered in the same physical form or concomitantly according to the above-described dosages and in the above-described delivery vehicles. The dosages for each active component can be measured separately and can be given as a single combined dose or given separately. They may be given at the same or at different times as long as both actives are in the patient at one time over a 24-hour period. Concomitant or concurrent administration means the patient takes one drug within about 5 minutes of taking the other drug. Because the goal is to provide rapid symptomatic relief to the patient, in most cases when treatment is started the two drugs would be administered to the patient close in time and typically concomitantly; thereafter, the timing of each drug's administration may not be as important.

The inventive composition is used to treat any of the diseases or disorders of the central nervous system. Such diseases and disorders are defined in The Diagnostic and Statistical Manual of Mental Disorders-IV (DSM-IV) (American Psychiatric Association (1995)). To the extent necessary for completion, the contents of this reference and all of the defined diseases or disorders are expressly incorporated by reference. Representative diseases or disorders include, but are not limited to the following: obesity, depression, schizophrenia, a stress related disease (e.g. general anxiety disorder), panic disorder, a phobia, obsessive compulsive disorder, post-traumatic-stress syndrome, immune system depression, incontinence, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, a movement disorder (e.g., Tourette's syndrome), oppositional defiant disorder, a pain disorder, peripheral neuropathy, post-traumatic stress disorder, premenstrual dysphoric disorder, a psychotic disorder, seasonal affective disorder, a sleep disorder, a specific developmental disorder, and selective serotonin reuptake inhibition (SSRI) "poop out" syndrome. Treatment of the above diseases or disorders is accomplished by delivering a therapeutically effective amount of the inventive composition to a mammal. In most cases this will be a human being, but treatment of food animals (e.g., livestock and poultry) and companion animals (e.g., dogs, cats and horses) is expressly covered herein.

In particular, the inventive composition is to be used in the treatment of schizophrenia. While not wishing to be bound to any specific scientific theory, it is believed that the addition of the norepinephrine reuptake inhibitor can significantly reduce the side effects associated with the neuroleptic treatments for schizophrenia.

The novel composition is expected to provide rapid relief to those suffering from the above diseases or disorders with a minimal amount of deleterious side effects. More specifically, the incidence of weight gain typically associated with the administration of atypical neuroleptic agents is minimized by the administration of the norepinephrine reuptake inhibitor.

The invention is described in greater detail by the following non-limiting example.

EXAMPLE 1

A pharmaceutical composition is prepared by combining reboxetine in either its racemic or +(S,S) entantiomeric form with a neuroleptic agent which is either: (a) clozapine, (b) olanzapine or (c) risperidone in a pharmaceutically acceptable carrier. The composition contains respective amounts of reboxetine and clozapine, olanzapine or risperidone to deliver on a daily basis between about 0.1 mg to about 10 mg reboxetine and between about (a): 25 to 500 mg clozapine; or (b) 0.05 to 30 mg olanzapine; or (c) 0.25 to 25 mg risperidone. The composition is administered to a patient for the treatment of schizophrenia on a daily, twice daily, three times daily, four times daily or six times daily basis.

EXAMPLE 2

A first pharmaceutical composition is prepared by combining reboxetine in either its racemic or +(S,S) enantiomeric form in a pharmaceutically acceptable carrier such that it can deliver between about 0.1 mg to about 10 mg reboxetine on a daily basis. A second pharmaceutical composition is prepared by combining either (a) clozapine, (b) olanzapine or (c) risperidone in a pharmaceutically acceptable carrier such that it can deliver between about (a): 25 to 500 mg clozapine; or (b) 0.05 to 30 mg olanzapine; or (c) 0.25 to 25 mg risperidone on a daily basis. The first composition is administered to a patient suffering from schizophrenia once, twice, three times, four times or six times daily such that the daily dosage is between about 0.1 to about 10 mg. The second composition is administered to the same patient at the same time as the administration of the first composition or any time within 24 hours of the administration of the first composition once, twice, three times, four times or six times daily such that the daily dosage is between about (a): 25 to 500 mg clozapine; or (b) 0.05 to 30 mg olanzapine; or (c) 0.25 to 25 mg risperidone. Alternatively, the second composition could first be administered, followed by the administration of the first composition as disclosed at the same time, or within 24 hours thereof.

EXAMPLE 3

Eleven mice per sample group are tested using a conditioned avoidance response assay, which can be used to predict the likelihood of possible detrimental side effects associated with the administration of a neuroleptic agent. The regimen included a pre-treatment with either saline or reboxetine (at a dosage of 6 mg/kg, i.p.) followed thirty minutes afterwards by treatment with either saline or raclopride (0.05 mg/kg or 0.10 mg/kg, s.c.). The mice are tested in the assay twenty minutes after administration of the saline or raclopride. The mean average avoidance as measured by the assay for the six different sample groups are as follows:

| SAMPLE | saline | 0.05 raclopride | 0.10 raclopride |
|---|---|---|---|
| saline | 100 | 90 | 70 |
| reboxetine (6 mg/kg) | 100 | 70 | 20 |

Having described the invention in detail and by reference to the preferred embodiments thereof, it will be apparent that modifications and variations are possible without departing from the scope of the appended claims.

What is claimed is:

1. A composition consisting essentially of:

(a) a pharmaceutically effective amount of reboxetine in its racemic or enantiomeric form; and (b) a pharmaceutically effective amount of one or more neuroleptic agents selected from the group consisting of clozapine, olanzapine, risperidone and mixtures thereof or a pharmaceutically effective salt thereof;

wherein components (a) and (b) are maintained in the same or in different delivery vehicles.

2. A composition according to claim 1 wherein said enantiomeric form is the +(S,S) enantiomeric form.

* * * * *